United States Patent
Watanabe et al.

(10) Patent No.: US 10,914,706 B2
(45) Date of Patent: Feb. 9, 2021

(54) GAS SENSOR

(71) Applicant: NGK INSULATORS, LTD., Nagoya (JP)

(72) Inventors: Yusuke Watanabe, Nagoya (JP); Takayuki Sekiya, Nisshin (JP); Yuki Nakayama, Nagoya (JP); Shota Kageyama, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 41 days.

(21) Appl. No.: 16/351,730

(22) Filed: Mar. 13, 2019

(65) Prior Publication Data

US 2019/0285574 A1    Sep. 19, 2019

(30) Foreign Application Priority Data

Mar. 16, 2018    (JP) .................. 2018-049437

(51) Int. Cl.
*G01N 27/407*    (2006.01)
*G01N 27/41*     (2006.01)
(Continued)

(52) U.S. Cl.
CPC .......... *G01N 27/41* (2013.01); *G01N 27/301* (2013.01); *G01N 27/307* (2013.01);
(Continued)

(58) Field of Classification Search
CPC .......... G01N 33/0037; G01N 27/4074; G01N 27/4075; G01N 27/41; G01N 27/4117
See application file for complete search history.

(56) References Cited

U.S. PATENT DOCUMENTS 5,763,763 A    6/1998  Kato et al.
6,071,393 A *  6/2000  Oshima .............. G01N 27/4074
                                                  204/425
(Continued)

FOREIGN PATENT DOCUMENTS

EP    0859223 A1 *  8/1998  .......... G01N 27/407
JP    3050781 B2    6/2000
(Continued)

OTHER PUBLICATIONS

Unexamined U.S. Appl. No. 16/351,562, filed Mar. 13, 2019.
Unexamined U.S. Appl. No. 16/351,741, filed Mar. 13, 2019.
Unexamined U.S. Appl. No. 16/351,565, filed Mar. 13, 2019.

*Primary Examiner* — Alexander S Noguerola
(74) *Attorney, Agent, or Firm* — Mattingly & Malur, PC

(57) ABSTRACT

A sensor element includes: a first inner space into which a measurement gas is introduced from outside; a second inner space communicated with the first inner space; a main pump cell constituted by an inner pump electrode facing the first inner space, an external pump electrode on a surface of the sensor element, and a solid electrolyte located therebetween; a measurement electrode facing the second inner space and functioning as a reduction catalyst for NOx; and a measurement pump cell constituted by the measurement electrode, the external pump electrode, and a solid electrolyte located therebetween. The inner pump electrode is a cermet made of an Au—Pt alloy containing Au ranging from 0.6 wt % to 1.4 wt % and $ZrO_2$, and has a thickness ranging from 5 μm to 30 μm, a porosity ranging from 5% to 40%, and an area ranging from 5 $mm^2$ to 20 $mm^2$.

5 Claims, 3 Drawing Sheets

(51) Int. Cl.
  *G01N 27/30* (2006.01)
  *G01N 27/409* (2006.01)
  *G01N 33/00* (2006.01)

(52) U.S. Cl.
  CPC ....... *G01N 27/409* (2013.01); *G01N 27/4072* (2013.01); *G01N 27/4075* (2013.01); *G01N 27/4076* (2013.01); *G01N 27/4077* (2013.01); *G01N 33/0037* (2013.01)

(56) References Cited

U.S. PATENT DOCUMENTS

| | | | |
|---|---|---|---|
| 2002/0108856 A1* | 8/2002 | Kunimoto | G01N 27/4071 204/425 |
| 2016/0033447 A1* | 2/2016 | Nakasone | G01N 27/301 204/427 |
| 2018/0202965 A1* | 7/2018 | Nakatou | G01N 27/419 |

FOREIGN PATENT DOCUMENTS

| | | | |
|---|---|---|---|
| JP | 2014-190940 A | 10/2014 | |
| JP | 2014-209128 A | 11/2014 | |

* cited by examiner

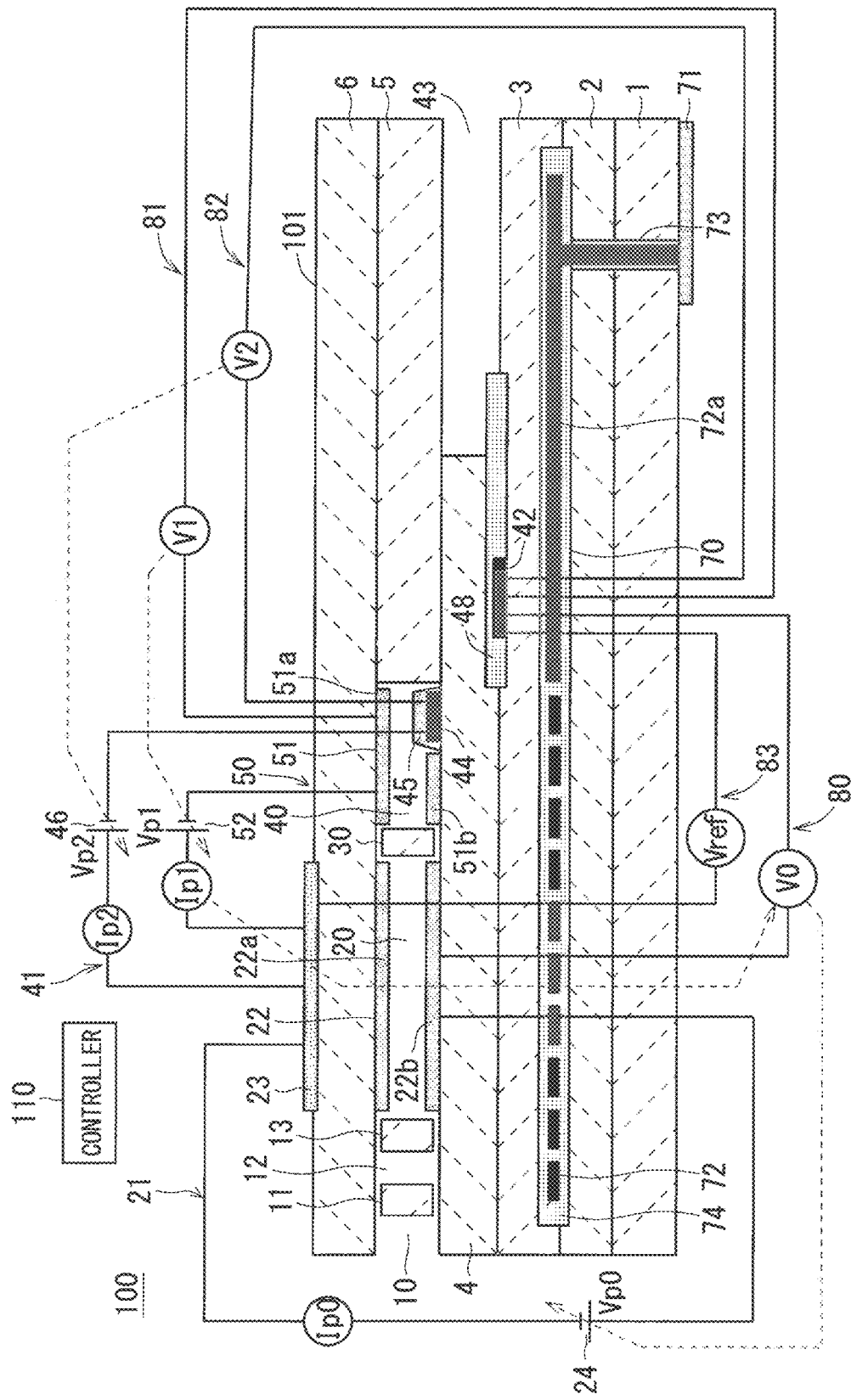
F I G. 1

GAS SENSOR

CROSS-REFERENCE TO RELATED APPLICATION

The present application claims priority from Japanese application JP 2018-049437 filed on Mar. 16, 2018, the contents of which is hereby incorporated by reference into this application.

BACKGROUND OF THE INVENTION

Field of the Invention

The present invention relates to a gas sensor obtaining a concentration of nitrogen oxide (NOx), and particularly to ensuring of accuracy in a high NOx concentration region.

Description of the Background Art

Already known is a limiting current type gas sensor (NOx sensor) using a sensor element which mainly has an oxygen ion conductive solid electrolyte as a constituent (for example, see Japanese Patent No. 3050781). In order to obtain the NOx concentration in such a gas sensor, a measurement gas is firstly introduced into a space provided inside the sensor element (an inner space) under a predetermined diffusion resistance, and oxygen in the measurement gas is pumped out in an electrochemical pump cell provided in two stages such as a main pump cell and an auxiliary pump cell (first and second electrochemical pump cells in Japanese Patent No. 3050781) to sufficiently lower the oxygen concentration in the measurement gas previously. Subsequently, NOx in the measurement gas is reduced or resolved in a measurement electrode functioning as a reduction catalyst (a third inner pump electrode in Japanese Patent No. 3050781), and oxygen generated by the reduction or the resolution is pumped out in an electrochemical pump cell including the measurement electrode other than the pump cell described above, called a measurement pump cell, for example (a third electrochemical pump cell in in Japanese Patent No. 3050781). The concentration of NOx is obtained by using a fact that current flowing in the measurement pump cell (NOx current) has a certain functional relationship with the concentration of NOx.

Also already known is an embodiment that in the gas sensor (NOx sensor), Pt to which Au is added (Au—Pt alloy) is used as a metal component of an inner pump electrode provided in an inner space to constitute a main pump cell, for purpose of suppressing the resolution of NOx when the main pump cell pumps oxygen out of the inner space and increasing a detection accuracy of NOx (for example, see Japanese Patent Application Laid-Open No. 2014-190940 and Japanese Patent Application Laid-Open No. 2014-209128).

In order to obtain the concentration of NOx in the measurement gas using the gas sensor described above, a functional relationship established between the NOx concentration and the NOx current needs to be previously specified at least in a concentration region assumed to be measured, using a plural types of model gas whose NOx concentrations are already known. For example, if the gas sensor is for obtaining the concentration of NOx in an exhaust gas emitted from an engine of a vehicle, it is expected to obtain the NOx concentration accurately to an extent of approximately 1500 ppm at a maximum.

If such a functional relationship is a simple linear relationship, at least two measurement points suffice to specify the functional relationship. However, in a conventional gas sensor, the functional relationship deviates from a form of a linear change in a range where the NOx concentration is high, in some cases. Many types of model gas having the different NOx concentrations need to be measured to accurately specify the functional relationship in such a gas sensor. From a viewpoint of an industrial mass production, it is preferable that the number of the measurement points is minimized to perform the measurement for specifying the functional relationship in a short amount of time. However, it is not necessarily clear in what type of gas sensor the deviation from the form of the linear change occurs in conventional cases.

As a matter of course, even if higher concentration NOx whose linearity is not ensured is measured using a gas sensor in which the functional relationship is specified using only a model gas within a concentration region where linearity is confirmed, the NOx concentration cannot be obtained accurately.

SUMMARY

The present invention relates to a gas sensor obtaining a concentration of nitrogen oxide, and particularly to ensuring of accuracy in a high NOx concentration region.

According to the present invention, a limiting current type gas sensor capable of specifying a concentration of NOx in a measurement gas includes: a sensor element formed of an oxygen ion conductive solid electrolyte, wherein the sensor element includes: a gas inlet into which a measurement gas is introduced from an outer space; a first inner space communicated with the gas inlet under a predetermined diffusion resistance; a second inner space communicated with the first inner space under a predetermined diffusion resistance; a main pump cell which is an electrochemical pump cell constituted by an inner pump electrode provided to face the first inner space, an external pump electrode provided on a surface of the sensor element, and the solid electrolyte located between the inner pump electrode and the external pump electrode; a measurement electrode provided to face the second inner space and covered with a porous protection film providing a predetermined diffusion resistance, said measurement electrode functioning as a reduction catalyst for NOx; an atmospheric air introduction layer into which atmospheric air is introduced from outside of the sensor element as a reference gas; a reference electrode covered with the atmospheric air introduction layer; and a measurement pump cell which is an electrochemical pump cell constituted by the measurement electrode, the external pump electrode, and a solid electrolyte located between the measurement electrode and the external pump electrode; and a concentration specifying element specifying a concentration of the NOx based on a magnitude of an NOx current flowing between the measurement electrode and the external pump electrode in the measurement pump cell, wherein the main pump cell is configured and disposed to pump out oxygen in the first inner space when a predetermined main pump voltage is applied between the inner pump electrode and the external pump electrode, and pumps out oxygen in the measurement gas introduced into the first inner space to lower oxygen partial pressure of the measurement gas in the first inner space, the measurement pump cell is configured and disposed to pump out oxygen near the measurement electrode when a predetermined pump voltage is applied between the inner pump electrode and the external pump electrode, and pumps out oxygen generated by a reduction of NOx in the measurement gas reaching near the measurement electrode in the measurement electrode, the inner pump electrode is a cermet electrode formed of an Au—Pt alloy containing Au equal to or larger than 0.6 wt % and equal to or smaller than 1.4 wt % and $ZrO_2$, and the inner pump electrode has a thickness ranging from 5 μm to 30 μm, a porosity ranging from 5% to 40%, and an area ranging from 5 $mm^2$ to 20 $mm^2$.

According to the present invention, even when the NOx concentration in the measurement gas is high, the resolution of NOx in the first inner space is suppressed, and linearity in sensitivity characteristics, which represents a functional relationship between a concentration of NOx in the measurement gas and an NOx current flowing in the measurement pump cell, is ensured.

Accordingly, an object of the present invention is to provide a gas sensor capable of measuring NOx accurately to an extent of a range where the NOx concentration is high.

These and other objects, features, aspects and advantages of the present invention will become more apparent from the following detailed description of the present invention when taken in conjunction with the accompanying drawings.

BRIEF DESCRIPTION OF THE DRAWINGS

FIG. 1 is a drawing schematically showing an example of a configuration of a gas sensor 100.

DESCRIPTION OF THE PREFERRED EMBODIMENTS

<Schematic Configuration of Gas Sensor>

Figure 2:
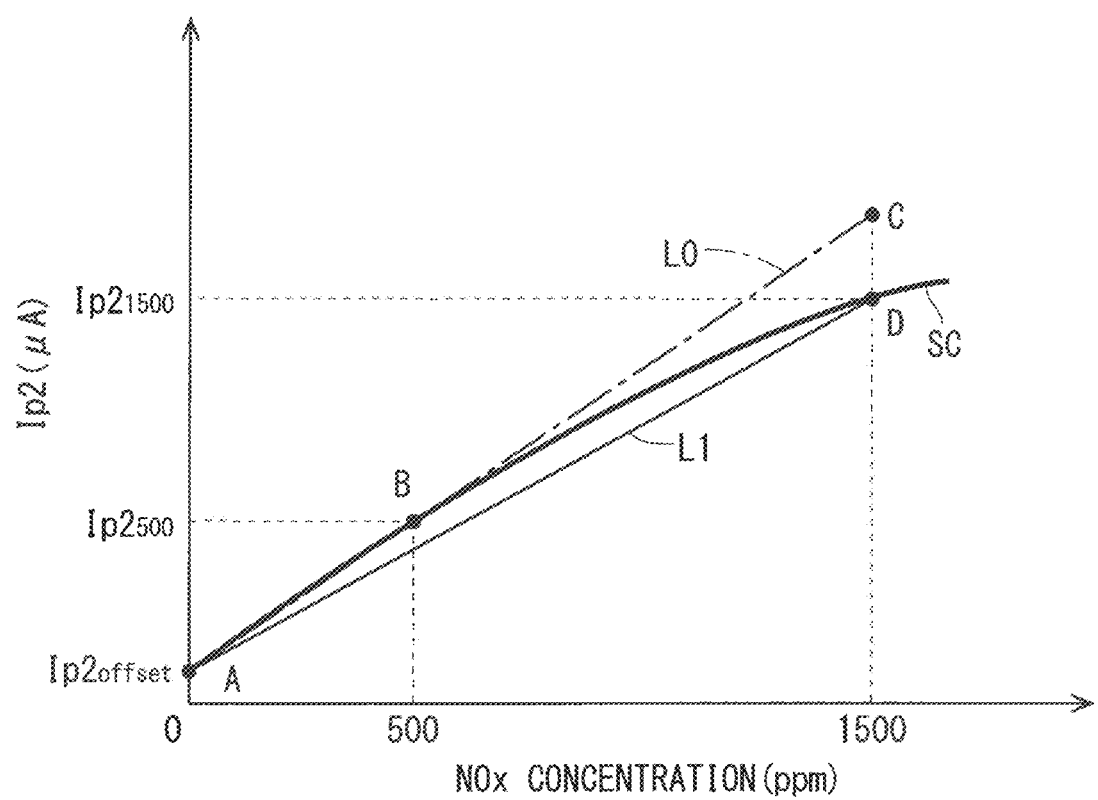
FIG. 2 is a drawing for describing a definition of a straight-line rate.

Described first is a schematic configuration of a gas sensor 100 including a sensor element 101 according to the present embodiment. In the present embodiment, the gas sensor 100 is a limiting current type NOx sensor which detects NOx using the sensor element 101 to measure a concentration of NOx.

FIG. 1 is a drawing schematically showing an example of a configuration of a gas sensor 100 including a vertical sectional view of the sensor element 101 along a longitudinal direction.

The sensor element 101 is a flat plate like (elongated plate like) element having a structure made up of six solid electrolyte layers of a first substrate layer 1, a second substrate layer 2, a third substrate layer 3, a first solid electrolyte layer 4, a spacer layer 5, and a second solid electrolyte layer 6, each of which is formed of zirconia ($ZrO_2$) which is an oxygen ion conductive solid electrolyte (for example, yttrium stabilized zirconia (YSZ)), laminated from a lower side in this order when seeing a drawing sheet of FIG. 1. The solid electrolyte forming these six layers is dense and airtight. In the subsequent description, a surface on an upper side of each of these six layers in FIG. 1 is simply referred to as an upper surface, and a surface on a lower side thereof is simply referred to as a lower surface in some cases. A whole part made of the solid electrolyte in the sensor element 101 is collectively referred to as a base part.

The sensor element 101 is manufactured by performing a predetermined processing and printing a circuit pattern on a ceramic green sheet corresponding to each layer, then laminating the green sheets, and further firing to integrate them with each other, for example.

A gas inlet 10, a first diffusion limiting part 11, a buffer space 12, a second diffusion limiting part 13, a first inner space 20, a third diffusion limiting part 30, and a second inner space 40 are adjacently formed to be communicated with each other in this order between a lower surface of the second solid electrolyte layer 6 and an upper surface of the first solid electrolyte layer 4 in one end of the sensor element 101.

The gas inlet 10, the buffer space 12, the first inner space 20, and the second inner space 40 are spaces in the sensor element 101 that look as if they were provided by hollowing out the spacer layer 5, an upper part thereof defined by the lower surface of the second solid electrolyte layer 6, a lower part thereof defined by the upper surface of the first solid electrolyte layer 4, and a side part thereof defined by the side surface of the spacer layer 5.

Each of the first diffusion limiting part 11, the second diffusion limiting part 13, and the third diffusion limiting part 30 is provided as two horizontally long slits (with an opening having a longitudinal direction perpendicular to the drawing sheet of FIG. 1). A region from the gas inlet 10 to the second inner space 40 is also referred to as a gas distribution part.

The first diffusion limiting part 11 and the second diffusion limiting part 13 are provided so that a diffusion resistance from the gas inlet 10 to an inner pump electrode 22 (described hereinafter) included in the first inner space 20 is equal to or larger than 200 $cm^{-1}$ and equal to or smaller than 1000 $cm^{-1}$.

A reference gas introduction space 43 is provided in a position farther away from an end side in relation to the gas introduction part between the upper surface of the third substrate layer 3 and the lower surface of the spacer layer 5, a side part thereof defined by a side surface of the first solid electrolyte layer 4. Atmospheric air, for example, is introduced into the reference gas introduction space 43 as a reference gas in measuring the NOx concentration.

An atmospheric air introduction layer 48 is a layer formed of porous alumina, and the reference gas is introduced into the atmospheric air introduction layer 48 through the reference gas introduction space 43. The atmospheric air introduction layer 48 is formed to cover a reference electrode 42.

The reference electrode 42 is an electrode having a configuration of being sandwiched between the upper surface of the third substrate layer 3 and the first solid electrolyte layer 4, and the atmospheric air introduction layer 48 leading to the reference gas introduction space 43 is provided around the reference electrode 42 as described above. An oxygen concentration (oxygen partial pressure) in the first inner space 20 and the second inner space 40 can be measured using the reference electrode 42 as described hereinafter.

The gas inlet 10 is a portion having an opening to an outer space in the gas introduction part, and the measurement gas is taken into the sensor element 101 from the outer space through the gas inlet 10.

The first diffusion limiting part 11 is a portion for providing the measurement gas taken from the gas inlet 10 of the predetermined diffusion resistance.

The buffer space 12 is a space provided for leading the measurement gas, which is introduced from the first diffusion limiting part 11, to the second diffusion limiting part 13.

The second diffusion limiting part 13 is a portion for providing the measurement gas introduced from the buffer space 12 to the first inner space 20 of the predetermined diffusion resistance.

In the introduction of the measurement gas from outside the sensor element 101 into the first inner space 20, the measurement gas rapidly taken into the sensor element 101 from the gas inlet 10 in accordance with a pressure variation of the measurement gas in the outer space (a pulsation of an exhaust gas pressure in a case where the measurement gas is an exhaust gas of a vehicle) is not directly introduced into the first inner space 20, but is introduced into the first inner space 20 after a concentration variation of the measurement gas is canceled through the first diffusion limiting part 11, the buffer space 12, and the second diffusion limiting part 13. Thus, the concentration variation of the measurement gas introduced into the first inner space 20 is substantially negligible.

The first inner space 20 is provided as a space for adjusting the oxygen partial pressure in the measurement gas introduced through the second diffusion limiting part 13. The oxygen partial pressure is adjusted by an operation of a main pump cell 21.

The main pump cell 21 is an electrochemical pump cell constituted by the inner pump electrode 22 having a ceiling electrode part 22a provided on almost the entire lower surface of the second solid electrolyte layer 6 facing the first inner space 20, an external pump electrode 23 provided to be exposed to the outer space in a region corresponding to the ceiling electrode part 22a on the upper surface of the second solid electrolyte layer 6 (one main surface of the sensor element 101), and the second solid electrolyte layer 6 sandwiched between the electrodes 22 and 23.

The inner pump electrode 22 is formed on the solid electrolyte layers on an upper side and a lower side defining the first inner space 20 (the second solid electrolyte layer 6 and the first solid electrolyte layer 4). Specifically, the ceiling electrode part 22a is formed on the lower surface of the second solid electrolyte layer 6 providing a ceiling surface of the first inner space 20, and a bottom electrode part 22b is formed on the upper surface of the first solid electrolyte layer 4 providing a bottom surface of the first inner space 20. The ceiling electrode part 22a and the bottom electrode part 22b are connected to each other in a conduction part provided on a sidewall surface (an inner surface) of the spacer layer 5 constituting both sidewall parts of the first inner space 20 (the illustration is omitted).

The ceiling electrode part 22a and the bottom electrode part 22b are provided to have a rectangular shape in a plan view. However, a configuration of providing only the ceiling electrode part 22a or only the bottom electrode part 22b may also be applicable.

Each of the inner pump electrode 22 and the external pump electrode 23 are formed as a porous cermet electrode. Particularly, the inner pump electrode 22 contacting the measurement gas is formed using a material whose reducing ability on an NOx component in the measurement gas is weakened. Specifically, the inner pump electrode 22 is formed as a cermet electrode made of an Au—Pt alloy and $ZrO_2$. A weight ratio of the Au—Pt alloy to $ZrO_2$ may be approximately Pt:$ZrO_2$=7.0:3.0 to 5.0:5.0. The detail of the inner pump electrode 22 is described hereinafter.

In the meanwhile, the external pump electrode 23 is formed to have a rectangular shape in a plan view as a cermet electrode made of Pt or a Pt alloy and $ZrO_2$, for example.

In the main pump cell 21, a desired pump voltage Vp0 is applied between the inner pump electrode 22 and the external pump electrode 23 by a variable source 24, and a pump current Ip0 is flowed between the inner pump electrode 22 and the external pump electrode 23 in a positive direction or a negative direction, thus oxygen in the first inner space 20 can be pumped out to the outer space or oxygen in the outer space can be pumped into the first inner space 20. The pump voltage Vp0 applied between the inner pump electrode 22 and the external pump electrode 23 in the main pump cell 21 is also referred to as the main pump voltage Vp0. The main pump cell 21 is preferably provided to have a minimum distance between the inner pump electrode 22 and the external pump electrode 23 of approximately 0.1 mm to 0.6 mm and an electrical resistance equal to or smaller than 150Ω.

The inner pump electrode 22, the second solid electrolyte layer 6, the spacer layer 5, the first solid electrolyte layer 4, the third substrate layer 3, and the reference electrode 42 constitute an electrochemical sensor cell, that is to say, a main-pump-control oxygen-partial-pressure detection sensor cell 80 to detect the oxygen concentration (oxygen partial pressure) in the atmosphere in the first inner space 20.

The oxygen concentration (oxygen partial pressure) in the first inner space 20 can be figured out by measuring an electromotive force V0 in the main-pump-control oxygen-partial-pressure detection sensor cell 80.

Furthermore, a feedback control is performed on the main pump voltage Vp0 so that the electromotive force V0 is set to constant, thus the pump current Ip0 is controlled. Accordingly, the oxygen concentration in the first inner space 20 is maintained to have a predetermined constant value.

The third diffusion limiting part 30 is a portion of providing the measurement gas, whose oxygen concentration (oxygen partial pressure) is controlled by an operation of the main pump cell 21 in the first inner space 20, of a predetermined diffusion resistance, and guiding the measurement gas to the second inner space 40.

The second inner space 40 is provided as a space for performing processing according to the measurement of nitrogen oxide (NOx) in the measurement gas introduced through the third diffusion limiting part 30. The NOx concentration is measured mainly in the second inner space 40 where the oxygen concentration is adjusted by an auxiliary pump cell 50, by an operation of a measurement pump cell 41. The oxygen concentration (oxygen partial pressure) is previously adjusted in the first inner space 20, and subsequently, in the second inner space 40, the adjustment of the oxygen partial pressure is further performed by the auxiliary pump cell 50 on the measurement gas introduced through the third diffusion limiting part 30. Accordingly, the oxygen concentration in the second inner space 40 can be accurately maintained constant, thus the gas sensor 100 enables the highly accurate NOx concentration measurement.

The auxiliary pump cell 50 is an auxiliary electrochemical pump cell constituted by an auxiliary pump electrode 51 having a ceiling electrode part 51a provided on almost the entire lower surface of the second solid electrolyte layer 6 facing the second inner space 40, the external pump electrode 23 (not limited to the external pump electrode 23 but an appropriate electrode outside the sensor element 101 is also applicable), and the second solid electrolyte layer 6.

The auxiliary pump electrode 51 is disposed in the second inner space 40 similarly to the inner pump electrode 22 provided in the first inner space 20 described above. In other words, the ceiling electrode part 51a is formed on the second solid electrolyte layer 6 providing a ceiling surface of the second inner space 40, and a bottom electrode part 51b is formed on the first solid electrolyte layer 4 providing a bottom surface of the second inner space 40. Each of the ceiling electrode part 51a and the bottom electrode part 51b has a rectangular shape in a plan view and is connected to each other in a conduction part provided on a sidewall surface (an inner surface) of the spacer layer 5 constituting both sidewall parts of the second inner space 40 (the illustration is omitted).

In the manner similar to the inner pump electrode 22, the auxiliary pump electrode 51 is also formed using a material whose reducing ability on an NOx component in the measurement gas is weakened.

In the auxiliary pump cell 50, a desired pump voltage Vp1 is applied between the auxiliary pump electrode 51 and the external pump electrode 23, thus oxygen in the atmosphere in the second inner space 40 can be pumped out to the outer space or oxygen can be pumped from the outer space into the second inner space 40.

The auxiliary pump electrode 51, the reference electrode 42, the second solid electrolyte layer 6, the spacer layer 5, the first solid electrolyte layer 4, and the third substrate layer 3 constitute an electrochemical sensor cell, that is to say, an auxiliary-pump-control oxygen-partial-pressure detection sensor cell 81 to control the oxygen partial pressure in the atmosphere in the second inner space 40.

The auxiliary pump cell 50 performs pumping with a variable source 52 on which a voltage control is performed based on an electromotive force V1 detected in the auxiliary-pump-control oxygen-partial-pressure detection sensor cell 81. Accordingly, the oxygen partial pressure in the atmosphere in the second inner space 40 is controlled so that it is low enough not to substantially influence the measurement of NOx.

In accordance with this, a pump current Ip1 thereof is used for controlling the electromotive force of the main-pump-control oxygen-partial-pressure detection sensor cell 80. Specifically, the pump current Ip1 is input, as a control signal, into the main-pump-control oxygen-partial-pressure detection sensor cell 80, and, through control of the electromotive force V0 thereof, the oxygen partial pressure in the measurement gas introduced through the third diffusion limiting part 30 into the second inner space 40 is controlled to have a gradient that is always constant. In using the gas sensor 100 as an NOx sensor, the oxygen concentration in the second inner space 40 is maintained to have a constant value of approximately 0.001 ppm by the functions of the main pump cell 21 and the auxiliary pump cell 50.

The measurement pump cell 41 measures the NOx concentration in the measurement gas in the second inner space 40. The measurement pump cell 41 is an electrochemical pump cell constituted by a measurement electrode 44 provided on the upper surface of the first solid electrolyte layer 4 facing the second inner space 40 in a position separated from the third diffusion limiting part 30, the external pump electrode 23, the second solid electrolyte layer 6, the spacer layer 5, and the first solid electrolyte layer 4.

The measurement electrode 44 is a porous cermet electrode. For example, the measurement electrode 44 is formed as a cermet electrode made of Pt or an alloy of Pt and $ZrO_2$. The measurement electrode 44 also functions as an NOx reduction catalyst for reducing NOx in the atmosphere in the second inner space 40. Furthermore, the measurement electrode 44 is covered with a fourth diffusion limiting part 45.

The fourth diffusion limiting part 45 is a film formed of a porous material mainly containing alumina ($Al_2O_3$). The fourth diffusion limiting part 45 has a function of limiting an amount of NOx flowing into the measurement electrode 44, and also functions as a protection film of the measurement electrode 44.

The measurement pump cell 41 can pump out oxygen generated by the resolution of NOx in the atmosphere around the measurement electrode 44 and detect a generation amount of oxygen as a pump current Ip2.

The second solid electrolyte layer 6, the spacer layer 5, the first solid electrolyte layer 4, the third substrate layer 3, the measurement electrode 44, and the reference electrode 42 constitute an electrochemical sensor cell, that is to say, a measurement-pump-control oxygen-partial-pressure detection sensor cell 82 to detect the oxygen partial pressure around the measurement electrode 44. A variable source is controlled based on an electromotive force 2 detected in the measurement-pump-control oxygen-partial-pressure detection sensor cell 82.

The measurement gas introduced into the second inner space 40 reaches the measurement electrode 44 through the fourth diffusion limiting part 45 under a condition where the oxygen partial pressure is controlled. NOx in the measurement gas around the measurement electrode 44 is reduced ($2NO \rightarrow N_2 + O_2$), and oxygen is generated. The generated oxygen is pumped by the measurement pump cell 41. At this time, a voltage Vp2 of the variable source 46 is controlled so that a control voltage V2 detected in the measurement pump control oxygen partial pressure detection sensor cell 82 is set to constant. Since the amount of oxygen generated around the measurement electrode 44 is proportional to the NOx concentration in the measurement gas, the NOx concentration in the measurement gas is calculated using the pump current Ip2 in the measurement pump cell 41. The pump current Ip2 is also referred to as the NOx current Ip2 hereinafter.

If the measurement electrode 44, the first solid electrolyte layer 4, the third substrate layer 3, and the reference electrode 42 are combined to constitute an oxygen-partial-pressure detection means as an electrochemical sensor cell, an electromotive force in accordance with a difference of an amount of oxygen generated by the reduction of the NOx component in the atmosphere around the measurement electrode 44 and an amount of oxygen contained in a reference atmosphere can be detected, and accordingly, a concentration of the NOx component in the measurement gas can be also obtained.

The second solid electrolyte layer 6, the spacer layer 5, the first solid electrolyte layer 4, the third substrate layer 3, the external pump electrode 23, and the reference electrode 42 constitute an electrochemical sensor cell 83, and the oxygen partial pressure in the measurement gas outside the sensor can be detected by an electromotive force Vref obtained by the sensor cell 83.

The sensor element 101 further includes a heater part 70 having a function of adjusting a temperature for heating sensor element 101 and keeping the temperature, in order to increase oxygen ion conductivity of the solid electrolyte constituting the base part.

The heater part 70 mainly includes a heater electrode 71, a heater element 72, a heater lead 72a, a through hole 73, and a heater insulating layer 74. The heater part 70 is embedded in the base part of the sensor element 101 except for the heater electrode 71.

The heater electrode 71 is an electrode formed to contact the lower surface of the first substrate layer 1 (the other main surface of the sensor element 101).

The heater element 72 is a resistance heating element provided between the second substrate layer 2 and the third substrate layer 3. The heater element 72 generates the heat by supplying power from the outside of the sensor element 101 via the heater electrode 71, the through hole 73, and the heater lead 72a which function as an energizing path. The heater element 72 is formed of Pt or mainly of Pt. The heater element 72 is embedded in a predetermined region in the sensor element 101 on a side including the gas introduction part so as to face the gas introduction part in a thickness direction of the element. The heater element 72 is provided to have a thickness of approximately 10 μm to 20 μm.

In the sensor element 101, the current is flowed into the heater element 72 via the heater electrode 71, thereby making the heater element 72 generate the heat, thus each part of the sensor element 101 can be heated to a predetermined temperature and kept to have the temperature. Specifically, the sensor element 101 is heated so that the temperature of the solid electrolyte and the electrode near the gas introduction part increases to approximately 700° C. to 900° C. The heating processing increases the oxygen ion conductivity of the solid electrolyte constituting the base part in the sensor element 101. The heating temperature at the time of heating by the heater element 72 in a case of using the gas sensor 100 (in a case of driving the sensor element 101) is referred to as a sensor element driving temperature.

The gas sensor 100 further includes a controller 110 controlling the operation of each part and specifying the NOx concentration based on the NOx current Ip2.

In the gas sensor 100 having such a configuration, oxygen contained in the measurement gas is pumped out through the operation of the main pump cell 21 and further of the auxiliary pump cell 50, and the measurement gas whose oxygen partial pressure is lowered enough not to substantially influence the measurement of NOx (for example, 0.0001 ppm to 1 ppm) reaches the measurement electrode 44. In the measurement electrode 44, NOx in the measurement gas which has reached the measurement electrode 44 is reduced, and oxygen is generated. The generated oxygen is pumped out by the measurement pump cell 41. The NOx current Ip2 flowing at the time of pumping out oxygen has a certain functional relationship with the concentration of NOx in the measurement gas (referred to as sensitivity characteristics hereinafter).

The sensitivity characteristics are previously specified using a plural types of model gas whose NOx concentrations are already known in advance of the actually use of the gas sensor 100, and data thereof is stored in the controller 110. In the actual use of the gas sensor 100, signals indicating a value of the NOx current Ip2 flowing in accordance with the NOx concentration in the measurement gas is provided to the controller 110 from moment to moment, and the NOx concentration is continuously calculated based on the value and the specified sensitivity characteristics and output in the controller 110. According to the gas sensor 100, the NOx concentration in the measurement gas can be obtained almost in real time.

The value of the NOx current Ip2 may also have dependence on the oxygen concentration in the measurement gas in some cases, and in such a case, it is also applicable to further increase the accuracy by obtaining the NOx concentration after correcting the NOx current Ip2 based on information indicating the oxygen concentration in the measurement gas (for example, the pump current Ip0 or the electromotive force $V_{ref}$) as necessary.

<Evaluation of Linearity in Sensitivity Characteristics>

As described above, the sensitivity characteristics of the gas sensor 100 is previously specified in advance to the actual use, however, such a specification is accompanied with the actual measurement using the model gas, thus it requires a certain amount of time. Thus, from a viewpoint of ensuring productivity for an industrial mass production, it is more preferable that the sensitivity characteristics have a relationship closer to a simple linear relationship (straight line relationship). It is because in such a case, the number of measurement points required for specifying the functional relationship can be reduced, and at least two measurement points (for example, a measurement in a state where the NOx concentration is 0 and a measurement in a state where the NOx concentration is sufficiently high) may suffice to specify the functional relationship.

In the present embodiment, a degree of linearity (straight line characteristics) of the sensitivity characteristics is evaluated by an index of a straight-line rate (unit: %). FIG. 2 is a drawing for describing a definition of the straight-line rate.

FIG. 2 shows a sensitivity characteristic SC in which a horizontal axis indicates the NOx concentration in the measurement gas (unit: ppm) and a vertical axis indicates the NOx current Ip2 (unit: μA). A point A in which the NOx concentration is 0 does not coincide with a coordinate origin by reason that the NOx current Ip2 for pumping out oxygen which is slightly existed and reaches the measurement electrode 44 flows in the measurement pump cell 41. This current is referred to as an offset current. In FIG. 2, a magnitude of the offset current is referred to as $Ip2_{offset}$.

If each pump cell included in the gas sensor 100 (more specifically, included in the sensor element 101) preferably operates, the sensitivity characteristic SC in the gas sensor 100 is deemed to be shown by substantially a straight line in a range from NOx concentration of 0 ppm (the point A) to at least approximately 500 ppm (a point B), as shown in FIG. 2. A value of the NOx current Ip2 in a state where the NOx concentration is 500 ppm is referred to as $Ip2_{500}$.

Ideally speaking, it is preferable that the sensitivity characteristics also maintain the linear form like a straight line L0 formed by further extending a line segment connecting the points A and B, for example, at a side of the high NOx concentration. However, as for the conventional gas sensor 100, in some cases, the actual sensitivity characteristic SC deviates from the linear change indicated by the straight line L0 as the NOx concentration increases, as illustrated in FIG. 2. It is considered because, in the case that the NOx concentration is high, NOx which is not originally supposed to be resolved until it reaches the measurement electrode 44 is resolved in the first inner space 20 in the operation of the main pump cell 21 for pumping out only oxygen, and as a result, the value of the NOx current Ip2 flowing in the measurement pump cell 41 in accordance with the NOx concentration gets smaller than the original value.

In the present embodiment, supposing that the gas sensor 100 is used on obtaining the NOx concentration in an exhaust gas emitted from an engine of a vehicle, the straight-line rate of the sensitivity characteristics is defined as described below, from a viewpoint of accurately obtaining the NOx concentration in the concentration region of 0 ppm to 1500 ppm, which is desired as the measurement concentration region in this supposition. The value of the NOx current Ip2 in a case where the NOx concentration is 1500 ppm is referred to as $Ip2_{1500}$, and a point for this case on the sensitivity characteristic SC is referred to as D.

The straight-line rate (%)=(a slope of a line segment $AD$/a slope of a line segment $AB$)×100    (1)

Herein,

The slope of the line segment AD=$(Ip2_{1500}-Ip2_{offset})/1500$ and

The slope of the line segment AB=$(Ip2_{500}-Ip2_{offset})/500$.

That is to say, a ratio of the slope of the line segment AD, indicated by a straight line L1 in FIG. 2, with respect to the slope of the line segment AB, which is a part of the sensitivity characteristic SC within the range of 500 ppm where the linearity is ensured, is defined as the straight-line rate. As the sensitivity characteristic Sc is closer to the straight line in the side of the high NOx concentration, the point D is closer to the point C, thus the value of the straight line obtained from the expression of (1) is close to 100%.

In the present embodiment, it is regarded that the sensitivity characteristic SC has the linearity in which the error thereof on the high NOx concentration is suppressed to fall within the allowable range in use when the straight-line rate is equal to or larger than 90%, and that the sensitivity characteristic SC has excellent linearity when the straight-line rate is equal to or larger than 95%, in the light of the measurement accuracy required for the gas sensor 100.

The straight-line rate can be evaluated through the measurement with the gas sensor 100 to be evaluated on the model gases having the NOx concentration in the measurement gas of 0 ppm, 500 ppm, and 1500 ppm, respectively, to obtain the NOx current Ip2.

This does not mean that the three types of the model gas described above are used when the sensitivity characteristic SC is specified prior to the actual use of the individual gas sensor 100. The model gas used when the sensitivity characteristic SC is specified may be selected in view of the usage mode assumed on the gas sensor 100, for example.

<Ensuring of Linearity of Sensitivity Characteristic>

Defined in the gas sensor 100 according to the present embodiment is a requirement satisfied by the inner pump electrode 22 constituting the main pump cell 21 and directly contacting the measurement gas, from a viewpoint that the resolution of NOx in the first inner space 20 is suppressed more reliably. Since a contribution from the conduction part regarding the resolution of NOx may be negligible, thus the term "inner pump electrode 22" indicates a part except for the conduction part in the following description.

In the gas sensor 100 according to the present embodiment, the inner pump electrode 22 satisfies first requirements (a1) to (d1) described hereinafter, thus the resolution of NOx in the first inner space 20 is suppressed even when the NOx concentration in the measurement gas is high. The suppression of this resolution is achieved, thus the linearity of the sensitivity characteristics is ensured to an extent of a range where the NOx concentration is high. Specifically, at least 90% or more of the straight-line rate is achieved.

(a1) Amount of Au: equal to or larger than 0.6 wt % and equal to or smaller than 1.4 wt %;

(b1) Thickness: equal to or larger than 5 μm and equal to or smaller than 30 μm;

(c1) Porosity: equal to or larger than 5% and equal to smaller than 40%;

(d1) Area: equal to or larger than 5 mm² and equal to or smaller than 20 mm².

The amount of Au indicates a weight ratio of Au in an AU—Pt alloy which is a metal component constituting the inner pump electrode 22. When the amount of Au exceeds 1.4 wt, Au is easily evaporated and scattered from the inner pump electrode 22 as a result of an exposure of the sensor element 101 to high temperature for a long period of time due to a continuous usage of the gas sensor 100. If the evaporated and scattered Au is adhered to the measurement electrode 44, a detection ability of NOx is lowered in the measurement pump cell 41, thus is not preferable.

If the amount of Au is smaller than 0.6 wt %, the thickness exceeds 30 μm, or the area exceeds 20 mm², NOx in the first inner space 20 is easily resolved, and the straight-line rate is lowered, thus is not preferable.

In the meanwhile, a lower limit of the thickness is set to 5 μm by reason that it is hard to control the thickness in a range smaller than 5 μm in a manufacturing process described hereinafter, and even when the inner pump electrode 22 is formed to have a desired thickness, the inner pump electrode 22 obtained in such a manner is inferior in long-term durability to that formed to have a thickness equal to or larger than 5 μm.

The case where the porosity exceeds 40% is not also preferable by reason that it is inferior in the long-term durability to a case where the porosity is set to equal to or smaller than 40%.

In the meanwhile, the condition where the porosity is smaller than 5% is not preferable by reason that a specific surface area decreases, thus a detection accuracy of the pump current Ip0 flowing in the main pump cell 21 is lowered and a response regarding the pumping out of oxygen is lowered.

Furthermore, the condition where the area is smaller than 5 mm² is not preferable by reason that an impedance of the main pump cell 21 increases and the detection accuracy of the pump current Ip0 is lowered, and the value of the main pump voltage Vp0 increases and NOx is easily resolved.

Even in a case where the inner pump electrode 22 includes only one of the ceiling electrode part 22a and the bottom electrode part 22b as described above, as long as the first requirements (a1) to (d1) described above are satisfied, the resolution of NOx in the first inner space 20 is suppressed.

Preferably, the inner pump electrode 22 is provided to further satisfy second requirements (a2) to (c2) described below, thus 95% or more of the straight-line rate is achieved and the sensitivity characteristic Sc of the gas sensor 100 has a higher level of linearity.

(a2) Amount of Au: equal to or larger than 0.7 wt % and equal to or smaller than 1.2 wt %;

(b2) Thickness: equal to or larger than 5 μm and equal to or smaller than 15 μm;

(c2) Porosity: equal to or larger than 5% and equal to smaller than 20%. The gas sensor 100 with the inner pump electrode 22 configured to satisfy the first requirements or further the second requirements as described above is used under a condition where a temperature of the inner pump electrode 22 is equal to or higher than 700° C. and equal to or lower than 900° C. by setting a sensor element driving temperature to equal to or higher than 700° C. and equal to or lower than 900° C. A condition where the temperature of the inner pump electrode 22 exceeds 900° C. is not preferable by reason that NOx in the first inner space 20 is easily resolved, thus the assumed straight-line rate is not ensured. The condition where the temperature is lower than 700° C. is not preferable by reason that an impedance of the main pump cell 21 increases and the detection accuracy of the pump current Ip0 is lowered, and the value of the main pump voltage Vp0 increases and NOx is easily resolved.

<Example of Setting Sensitivity Characteristic>

When the sensitivity characteristic SC is specified prior to the actual use of the gas sensor 100 satisfying the first requirements (a1) to (d1) or further satisfying the second requirements (a2) to (c2) described above, the model gas to be used may be selected in view of the usage mode assumed on the gas sensor 100, for example.

In the case that the measurement accuracy on a low NOx concentration is more important than that on a high NOx concentration, the sensitivity characteristic SC may be specified using a model gas having an NOx concentration of 0 ppm and a model gas having an NOx concentration of several hundred ppm (for example, 500 ppm), for example. In this case, also as can be seen from FIG. 2, the excellent measurement accuracy is ensured in the range of the low NOx concentration, however, a gap increases between the actual sensitivity characteristic SC and the specified sensitivity characteristic SC as the NOx concentration gets higher, and this gap appears as an error in the measurement accuracy.

In contrast, in the case the NOx concentration is required to be specified with substantially a similar degree of accuracy over a whole measured object concentration region, the sensitivity characteristic SC may be specified using a model gas having an NOx concentration of 0 ppm and a model gas having an NOx concentration of a thousand and several hundred ppm (for example, 1500 ppm), for example. In this case, the specified sensitivity characteristic SC forms a line like the straight line L1 in FIG. 2, and deviates from the actual sensitivity characteristic SC over the whole measured object concentration region, however, a significant difference hardly occurs in the gap in accordance with the NOx concentration.

In both cases, the error falls within an allowable range which is previously assumed as long as the gas sensor 100 is configured so that the straight-line rate is equal to or larger than 90%, or equal to or larger than 95%.

<Manufacturing Process of Sensor Element>

Described next is a process of manufacturing the sensor element 101 having the configuration and the feature described above. In the present embodiment, the sensor element 101 is manufactured by forming a laminated body formed of green sheets containing an oxygen ion conductive solid electrolyte such as zirconia as a ceramic component, and then cutting and firing the laminated body.

Figure 3:
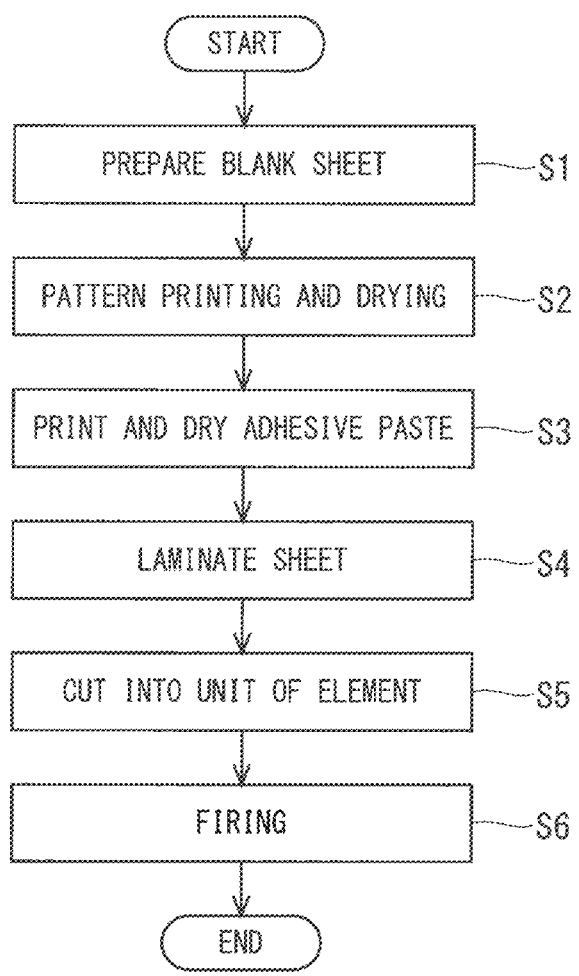
FIG. 3 is a drawing showing a flow of processing in manufacturing a sensor element 101.

Described hereinafter as an example is a case of manufacturing the sensor element 101 including the six layers illustrated in FIG. 1. Prepared in such a case are six green sheets corresponding to the first substrate layer 1, the second substrate layer 2, the third substrate layer 3, the first solid electrolyte layer 4, the spacer layer 5, and the second solid electrolyte layer 6. FIG. 3 is a drawing showing a flow of processing in manufacturing a sensor element 101.

In manufacturing the sensor element 101, firstly, a blank sheet (not shown) which is a green sheet on which no pattern is formed is prepared (Step S1). When the sensor element 101 including the six layers is manufactured, six blank sheets are prepared to correspond to each layer. The blank sheets have plurality of sheet holes used for alignment in performing a printing and laminating the sheets. The sheet hole is previously formed in the blank sheet through, for example, punching processing using a punching device in a stage prior to the pattern formation. Green sheets corresponding to layers including the inner spaces also include penetrating portions corresponding to the inner spaces, which are also provided by the similar punching processing previously. A thickness of each blank sheet corresponding to each layer of the sensor element 101 needs not be the same as each other.

After the blank sheet corresponding to each layer is prepared, the pattern printing and dry processing are performed on each blank sheet (Step S2). Formed specifically are patterns of various types of electrodes, a pattern of the fourth diffusion limiting part 45, patterns of the heater element 72 and the heater insulating layer 74, and a pattern of an inner wiring not shown in the drawings. An application or a placement of a sublimation material for forming the first diffusion limiting part 11, the second diffusion limiting part 13, and the third diffusion limiting part 30 is also performed at a timing of the pattern printing.

The printing of each pattern is performed by applying a pattern formation paste prepared in accordance with characteristics required for each formation object on the blank sheet using a known screen printing technique. A known drying means can be used for drying processing after the printing.

Particularly, the paste for forming the inner pump electrode 22 is prepared so that the finally obtained inner pump electrode 22 satisfies at least the first requirements (a1) to (d1), preferably the second requirements (a2) to (c2), and is applied.

After the pattern printing on each blank sheet is finished, processing of printing and drying an adhesive paste for laminating and attaching the green sheet corresponding to each layer on and to one another is performed (Step S3). A known screen printing technique can be used for printing the adhesive paste, and a known drying means can be used for drying processing after the printing.

Subsequently, the green sheets on which an adhesive agent has been applied are stacked in a predetermined order, and the stacked green sheets are crimped under a predetermined temperature condition and pressure condition to form one laminated body (Step S4). Specifically, the crimping is performed by stacking and holding the green sheets to be laminated on a predetermined laminating jig not shown while aligning the green sheets using the sheet holes, and then heating and pressurizing the green sheets together with the laminating jig using a laminating machine such as a known oil hydraulic pressing machine. The pressure, the temperature, and the time for heating and pressurizing depend on the laminating machine to be used, however, an appropriate condition may be determined to be able to achieve a favorable lamination.

When the laminated body is obtained as described above, subsequently, the laminated body is cut out at a plurality of locations to obtain an individual unit (referred to as the element body) of the sensor element 101 (Step S5).

The firing is performed on the element body at a firing temperature of approximately 1300° C. to 1500° C. (Step S6). The sensor element 101 is thereby manufactured. In other words, the sensor element 101 is manufactured through integrally firing the solid electrolyte and the electrode. The firing temperature is preferably set to 1200° C. to 1500° C. (for example, 1400° C.). The integrated firing is performed in the above manner, thus each electrode has sufficient adhesion strength in the sensor element 101.

The sensor element 101 obtained in such a manner is stored in a predetermined housing, and incorporated into a main body (not shown) of the gas sensor 100.

EXAMPLE

Seventeen types of gas sensors 100 (No. 1 to No. 17) each having different combination of the amount of Au, the thickness, the porosity, and the area of the inner pump electrode 22 were manufactured, and the straight-line rate of each sensitivity characteristics was obtained based on the expression (1) and the linearity thereof was evaluated. The sensor element driving temperature on obtaining the sensitivity characteristics was set to 830° C.

Specifically, the amount of Au, the thickness, the porosity, and the area are varied as described hereinafter.

Amount of Au: seven levels of 0.0 wt %, 0.5 wt %, 0.6 wt %, 0.8 wt %, 1.0 wt %, 1.3 wt %, and 1.4 wt %;

Thickness: five levels of 10 μm, 15 μm, 20 μm, 30 μm, and 40 μm;

Porosity: eight levels of 15%, 16%, 17%, 18%, 20%, 30%, 40%, and 50%;

Area: six levels of 4.0 mm$^2$, 6.0 mm$^2$, 7.6 mm$^2$, 10.0 mm$^2$, 20 mm$^2$, and 25 mm$^2$;

Table 1 shows the condition of the inner pump electrode 22 and an evaluation result of the linearity of the sensitivity characteristics on each gas sensor 100. All of the gas sensors 100 of No. 1 to No. 11 include the inner pump electrode 22 satisfying all of the first requirements (a1) to (d1). In the meanwhile, the gas sensors 100 of No. 12 and No. 13 do not satisfy the requirement (a1), the gas sensor 100 of No. 14 does not satisfy the requirement (c1), the gas sensors 100 of No. 15 and No. 16 do not satisfy the requirement (d1), and the gas sensor 100 of No. 17 does not satisfy the requirement (b1).

TABLE 1

| | Inner pump electrode | | | | |
|---|---|---|---|---|---|
| NO. | Amount of Au [wt %] | Thickness [μm] | Porosity [%] | Area [mm$^2$] | Determination |
| 1 | 0.8 | 15 | 15 | 7.6 | ○ |
| 2 | 1.0 | 10 | 15 | 7.6 | ○ |
| 3 | 0.6 | 15 | 17 | 7.6 | Δ |
| 4 | 1.0 | 15 | 40 | 7.6 | Δ |
| 5 | 0.8 | 30 | 15 | 7.6 | Δ |
| 6 | 1.0 | 20 | 16 | 7.6 | ○ |
| 7 | 1.4 | 20 | 30 | 7.6 | Δ |
| 8 | 1.0 | 10 | 15 | 6.0 | ○ |
| 9 | 1.3 | 15 | 18 | 7.6 | Δ |
| 10 | 1.0 | 15 | 20 | 10.0 | ○ |
| 11 | 1.0 | 15 | 10 | 20.0 | ○ |
| 12 | 0.0 | 20 | 15 | 7.6 | X |
| 13 | 0.5 | 15 | 20 | 7.6 | X |
| 14 | 1.0 | 15 | 50 | 7.6 | X |
| 15 | 1.0 | 15 | 14 | 4.0 | X |
| 16 | 0.8 | 20 | 20 | 25.0 | X |
| 17 | 1.0 | 40 | 15 | 7.6 | X |

The linearity is evaluated as follows.

Firstly, the gas sensor 100 having the value of the straight-line rate equal to or larger than 95% and equal to and smaller than 100% is determined to have the excellent linearity, and denoted by "○" (circle) in an item of "Determination" of the corresponding gas sensor 100 in Table 1.

The gas sensor 100 having the value of the straight-line rate equal to or larger than 90% and smaller than 95% is determined to have the linearity to the extent that the error of the sensitivity characteristics on the high NOx concentration is suppressed within the allowable range in use, and denoted by "Δ" (triangle) in an item of "Determination" of the corresponding gas sensor 100 in Table 1.

In the meanwhile, the gas sensor 100 having the straight-line rate smaller than 90% is determined that the sufficient linearity is not obtained, and denoted by "×" (cross mark) in an item of "Determination" of the corresponding gas sensor 100 in Table 1.

As illustrated in Table 1, in the gas sensors 100 of No. 1 to No. 11 including the inner pump electrode 22 satisfying all of the first requirements (a1) to (d1), the straight-line rate of 90% or more was obtained, however, in the gas sensors 100 of No. 12 to No. 17 including the inner pump electrode 22 which does not satisfy one of the first requirements (a1) to (d1), the straight-line rate was smaller than 90%.

The result shows that the linearity in the sensitivity characteristics of the gas sensor 100 is ensured to be allowable in light of the measurement accuracy by making the inner pump electrode 22 satisfy all of the first requirements (a1) to (d1).

In addition, in all of the gas sensors 100 of No. 1, No. 2, No. 6, No. 8, No. 10, and No. 11 including the inner pump electrode 22 satisfying all of the second requirements (a2) to (c2), 95% or more of the straight-line rate was obtained.

The result shows that the gas sensor 100 having the sensitivity characteristics of the excellent linearity is achieved by making the inner pump electrode 22 satisfy all of the second requirements (a2) to (c2) in addition to the first requirements (a1) to (d1).

While the invention has been shown and described in detail, the foregoing description is in all aspects illustrative and not restrictive. It is therefore understood that numerous modifications and variations can be devised without departing from the scope of the invention.

What is claimed is:

1. A limiting current type gas sensor capable of specifying a concentration of NOx in a measurement gas, comprising
a sensor element formed of an oxygen ion conductive solid electrolyte, wherein said sensor element includes:
a gas inlet into which a measurement gas is introduced from an outer space;
a first inner space communicated with said gas inlet under a predetermined diffusion resistance;
a second inner space communicated with said first inner space under a predetermined diffusion resistance;
a main pump cell which is an electrochemical pump cell constituted by an inner pump electrode provided to face said first inner space, an external pump electrode provided on a surface of said sensor element, and said solid electrolyte located between said inner pump electrode and said external pump electrode;
a measurement electrode provided to face said second inner space and covered with a porous protection film providing a predetermined diffusion resistance, said measurement electrode functioning as a reduction catalyst for NOx;
a reference electrode which contacts atmospheric air which is introduced from outside of said sensor element as a reference gas; and
a measurement pump cell which is an electrochemical pump cell constituted by said measurement electrode, said external pump electrode, and said solid electrolyte located between said measurement electrode and said external pump electrode; and
a controller which receives signals corresponding to a magnitude of an NOx current flowing between said measurement electrode and said external pump electrode in said measurement pump cell and specifies a concentration of said NOx based on the magnitude of the NOx current, wherein
said main pump cell is configured and disposed to pump out oxygen in said first inner space when a predetermined main pump voltage is applied between said inner pump electrode and said external pump electrode, and pumps out oxygen in said measurement gas introduced into said first inner space to lower oxygen partial pressure of said measurement gas in said first inner space,
said measurement pump cell is configured and disposed to pump out oxygen near said measurement electrode when a predetermined pump voltage is applied between said inner pump electrode and said external pump electrode, and pumps out oxygen generated by a reduction of NOx in said measurement gas reaching near said measurement electrode in said measurement electrode, said inner pump electrode is a cermet electrode formed of an Au—Pt alloy containing Au equal to or larger than 0.6 wt % and equal to or smaller than 1.4 wt % and $ZrO_2$, and said inner pump electrode has a thickness ranging from 5 μm to 30 μm, a porosity ranging from 5% to 40%, and an area ranging from 5 $mm^2$ to 20 $mm^2$.

2. The gas sensor according to claim 1, wherein said inner pump electrode is a cermet electrode made of an Au—Pt alloy containing Au equal to or larger than 0.7 wt % and equal to or smaller than 1.2 wt % and $ZrO_2$, and said inner pump electrode has a thickness ranging from 5 μm to 15 μm and a porosity ranging from 5% to 20%.

3. The gas sensor according to claim 2, wherein said sensor element further includes:
  a main pump control sensor cell which is an electrochemical sensor cell constituted by said inner pump electrode, said reference electrode, and said solid electrolyte located between said inner pump electrode and said reference electrode;
  an auxiliary pump cell which is an electrochemical pump cell constituted by an auxiliary pump electrode provided to face said second inner space, said external pump electrode, and said solid electrolyte located between said auxiliary pump electrode and said external pump electrode;
  an auxiliary-pump-control sensor cell which is an electrochemical sensor cell constituted by said auxiliary pump electrode, said reference electrode, and said solid electrolyte located between said auxiliary pump electrode and said reference electrode; and
  a measurement-pump-control sensor cell which is an electrochemical sensor cell constituted by said measurement electrode, said reference electrode, and said solid electrolyte located between said measurement electrode and said reference electrode, wherein when said main pump cell pumps out oxygen in said measurement gas located in said first inner space, said main pump voltage in accordance with an electromotive force generated between said inner pump electrode and said reference electrode in said main pump control sensor cell is applied between said inner pump electrode and said external pump electrode, said auxiliary pump cell is configured and disposed to pump out oxygen in said measurement gas introduced into said second inner space when a pump voltage in accordance with an electromotive force generated between said auxiliary pump electrode and said reference electrode in said auxiliary pump control sensor cell is applied between said auxiliary pump electrode and said external pump electrode, said measurement gas whose oxygen partial pressure has been further lowered compared to oxygen partial pressure in said first inner space through pumping out oxygen with said auxiliary pump cell reaches said measurement electrode, and when said measurement pump cell pumps out oxygen generated in said measurement electrode, a pump voltage in accordance with an electromotive force generated between said measurement electrode and said reference electrode in said measurement pump control sensor cell is applied between said measurement electrode and said external pump electrode.

4. The gas sensor according to claim 1, wherein said sensor element further includes:
  a main-pump-control sensor cell which is an electrochemical sensor cell constituted by said inner pump electrode, said reference electrode, and said solid electrolyte located between said inner pump electrode and said reference electrode;
  an auxiliary pump cell which is an electrochemical pump cell constituted by an auxiliary pump electrode provided to face said second inner space, said external pump electrode, and said solid electrolyte located between said auxiliary pump electrode and said external pump electrode;
  an auxiliary-pump-control sensor cell which is an electrochemical sensor cell constituted by said auxiliary pump electrode, said reference electrode, and said solid electrolyte located between said auxiliary pump electrode and said reference electrode; and
  a measurement-pump-control sensor cell which is an electrochemical sensor cell constituted by said measurement electrode, said reference electrode, and said solid electrolyte located between said measurement electrode and said reference electrode, wherein when said main pump cell pumps out oxygen in said measurement gas located in said first inner space, said main pump voltage in accordance with an electromotive force generated between said inner pump electrode and said reference electrode in said main-pump-control sensor cell is applied between said inner pump electrode and said external pump electrode, said auxiliary pump cell is configured and disposed to pump out oxygen in said measurement gas introduced into said second inner space when a pump voltage in accordance with an electromotive force generated between said auxiliary pump electrode and said reference electrode in said auxiliary pump control sensor cell is applied between said auxiliary pump electrode and said external pump electrode, said measurement gas whose oxygen partial pressure has been further lowered compared to oxygen partial pressure in said first inner space through pumping out oxygen with said auxiliary pump cell reaches said measurement electrode, and when said measurement pump cell pumps out oxygen generated in said measurement electrode, a pump voltage in accordance with an electromotive force generated between said measurement electrode and said reference electrode in said measurement-pump-control sensor cell is applied between said measurement electrode and said external pump electrode.

5. The gas sensor according to claim 1, further comprising an atmospheric air introduction layer covering the reference electrode and into which the atmospheric air is introduced from the outside of said sensor element as the reference gas.

* * * * *